US006327328B1

(12) United States Patent
Satoh et al.

(10) Patent No.: US 6,327,328 B1
(45) Date of Patent: Dec. 4, 2001

(54) COMPUTERIZED TOMOGRAPHY SYSTEM (75) Inventors: Katsutoshi Satoh, Hitachi; Shigeru Izumi, Tokyo, both of (JP)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 09/339,931

(22) Filed: Jun. 25, 1999

(30) Foreign Application Priority Data

Jun. 26, 1998 (JP) .................................................. 10-179977

(51) Int. Cl.[7] .................................................. G01N 23/00
(52) U.S. Cl. .................................................. 378/17; 378/20
(58) Field of Search ........................................ 378/20, 17

(56) References Cited

U.S. PATENT DOCUMENTS 4,555,760 * 11/1985 Op de Beek et al. .................. 378/17
4,600,998 * 7/1986 Huet ...................................... 378/20
4,872,187 * 10/1989 Nakahata et al. ...................... 378/17
5,119,408    6/1992 Little et al. .
5,493,593    2/1996 Müller .

FOREIGN PATENT DOCUMENTS 0 471 096 A1    2/1992 (EP) .
0 652 433 A1    5/1995 (EP) .
2 232 332 A    12/1990 (GB) .

* cited by examiner

Primary Examiner—Craig E. Church
(74) Attorney, Agent, or Firm—Antonelli, Terry, Stout & Kraus, LLP

(57) ABSTRACT

An X ray CT system wherein radiation is irradiated on an object to be inspected during rotation of the object to obtain image data, in which case a rotary center of the object is set at a plurality of different positions in an angle of an angular pitch angle of radiation detectors for each turn, and a tomographic image is reconstructed from data on the X-ray passed through the objected obtained by rotating the object by a polurality of turns.

6 Claims, 8 Drawing Sheets

COMPUTERIZED TOMOGRAPHY SYSTEM

BACKGROUND OF THE INVENTION

The present invention relates to computerized tomography systems and more particularly, to a computerized tomography system and method which can suitably take a tomographic image in a transversal plane of an object to be inspected with use of X ray.

A computerized tomography system (X-ray computed tomography (CT) system or X ray CT system) using X ray, which takes a tomographic image in a transversal plane of an object to be inspected, includes an X ray source for emitting an X ray, a detection device for detecting the X ray and a computer for creating a tomographic image. In particular, the detection device comprises, in many cases, an array detection device made up of a multiplicity of X ray detectors arrayed in a row. The X ray detectors of the array detection device are arranged to detect the X ray emitted from the single X ray source. In such an X ray CT system, especially employing a tomography called a third generation system, in order to increase the spatial resolution of a tomographic image, it is necessary to narrow an array interval or pitch between the X ray detectors of the array detection device.

However, the array detection device has its limitation on making narrow the array pitch between the X ray detectors of the array detection device, because the X ray detectors have a limited size. For example, when each X ray detector has a transverse width of 1 mm, it is impossible to make the pitch between the X ray detectors of the array detection device to be 1 mm or smaller. Accordingly, there has been demanded such a tomography system which can increase the spatial resolution of a tomographic image while eliminating the need for narrowing the array pitch between the X ray detectors of the array detection device.

In such an X ray CT system disclosed in JP-A-62-116238, a relative positional relationship between an X ray source and an array detection device is made variable in a range of interval or pitch between X ray detectors of the array detection device, thus enabling increase of a spatial resolution of an tomographic image while eliminating the need for physically narrowing the array pitch of the X ray detectors.

In the case of an X ray CT system wherein a collimator having slits for passage of an X ray is provided in front of the X ray detectors of the array detection device (on a side of an X ray source), however, it is impossible to employ such a technique as disclosed in the above JP-A. This is because the slits provided in front of the X ray detectors are positioned to face the single X ray source, so that a shift in the relative positional relationship between the X ray source and X ray detectors causes the X ray not to be directed on the X ray detectors.

SUMMARY OF THE INVENTION

It is therefore an object of the present invention to provide a computerized tomography system which can realize an increase in the spatial resolution of a tomographic image.

In accordance with a first aspect of the present invention, the above object is attained by providing a computerized tomography system which includes a radiation source for emitting a radiation onto an object to be inspected, a rotary table for carrying the object to be inspected thereon to rotate the object to be inspected, a collimator having a plurality of through-holes for passage of the radiation passed through the object to be inspected, a plurality of radiation detectors disposed as opposed to the associated through-holes for detecting the radiation passed through the through-holes, a unit for setting the rotary center of the rotary table at positions different for every one rotation of the object to be inspected, and a unit for reconstructing a tomographic image in one transversal plane on the basis of detection signals of the plurality of radiation detectors obtained by irradiating the radiation on the object to be inspected while rotating the object to be inspected.

In the first aspect, a plurality of rotary center positions of the rotary table are set for one transversal plane of the object to be inspected, and the unit for reconstructing the tomographic image for one transversal plane of the object to be inspected is provided with use of the detection signals of the radiation detectors obtained by rotating the rotary table with the respective rotary center positions. Therefore, for the reconstruction of the tomographic image for one transversal plane of the object to be inspected, the detection signals of the radiation detectors detected with the interval substantially narrower than the array pitch of the radiation detectors can be used. This can lead to an improvement in the spatial resolution of the tomographic image.

In accordance with a second aspect of the present invention, the above object is attained by a computerized tomography system which includes a pivoting truck, a radiation source provided to said pivoting truck for emitting radiation toward an object to be inspected, a table disposed inside of the pivoting truck for mounting the object to be inspected thereon, a collimator having a plurality of through-holes for passage of the radiation passed through the object to be inspected and provided to the pivoting truck, a plurality of radiation detectors disposed to the pivoting truck as opposed to the through-holes for detecting the radiation passed through the through-holes, a unit for setting the radiation source and radiation detectors at different positions in an array direction of the radiation detectors for each turn according to the number of turns of the pivoting truck which is necessary for obtaining a tomographic image of a transversal plane of the object to be inspected, and a unit for reconstructing a tomographic image of the transversal plane by using digital signals of the plurality of radiation detectors obtained by irradiating the radiation on the object to be inspected during rotation of the pivoting truck for a plurality of set positions of the radiation source and radiation detectors.

Even in this case, for the reconstruction of the tomographic image for one transversal plane of the object to be inspected, the detection signals of the radiation detectors detected with the interval substantially narrower than the array pitch of the radiation detectors can be used. Thus this can lead to an improvement in the spatial resolution of the tomographic image.

DESCRIPTION OF THE EMBODIMENTS

Figure 1A:
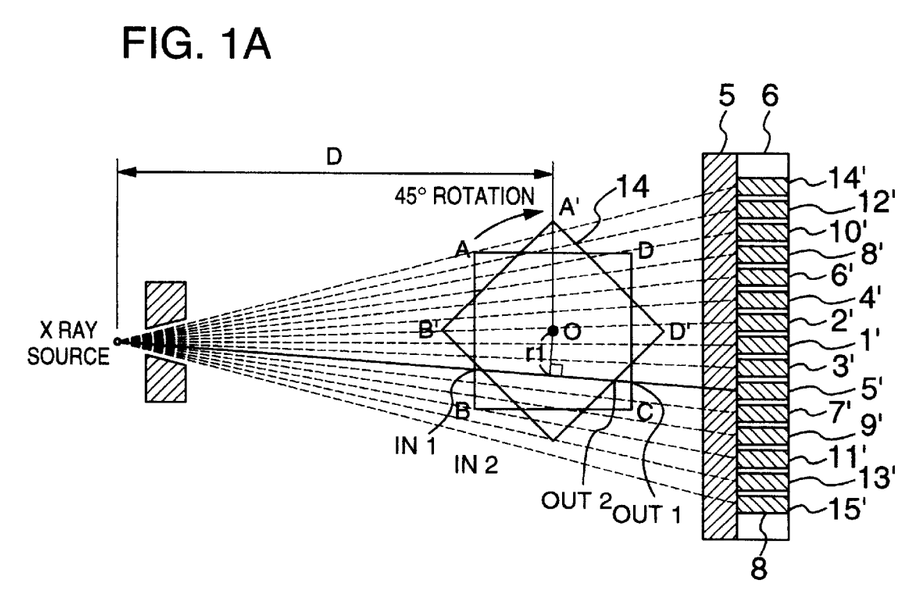
FIGS. 1A to 1D are diagrams for explaining the principle of the present invention.

FIG. 1A shows the principle of the present invention. In the drawing, a radiation is radially emitted from an X ray source 1 toward an object 14 to be inspected. The radiation is passed through slits in a collimator 5 and detected by detectors 8 (actually numbered 1' to 15' in the drawing) collectively constituting an X ray array detection device 6. The checking object is placed on a rotary table and rotated while receiving the radiation.

Figure 1B:
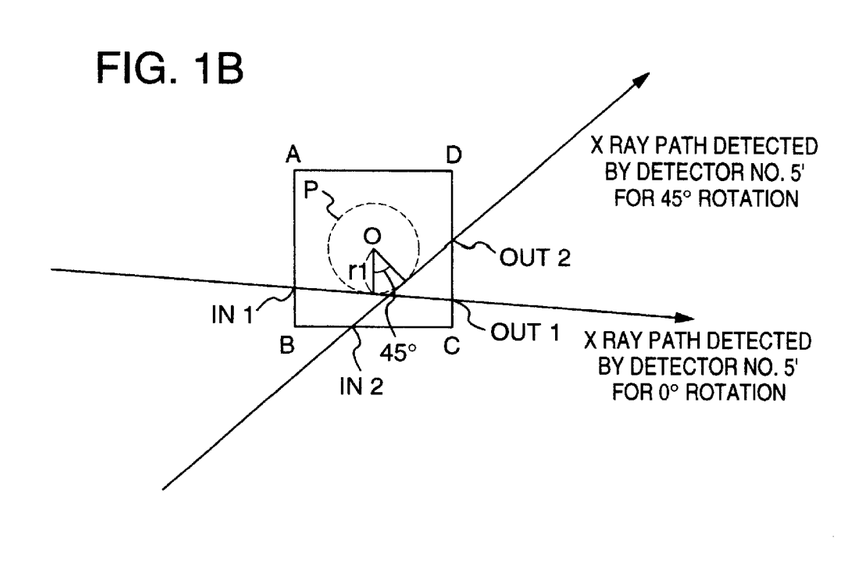
Figure 1C:
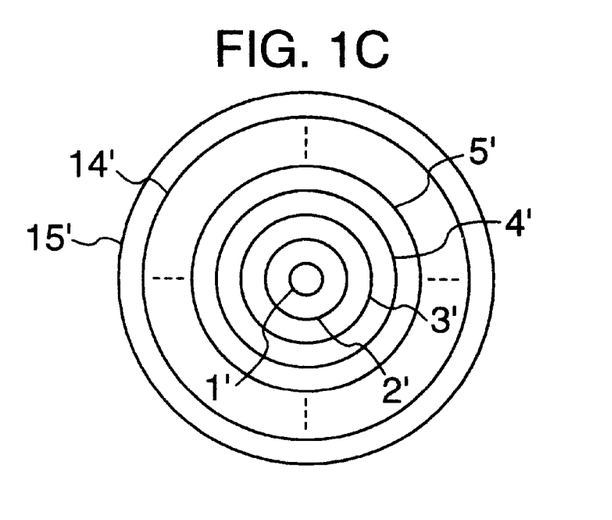

When attention is now paid to the detector 5', as shown in FIG. 1B, the detector 5' detects the radiation passed through the object along a line IN1-OUT1 when a rotation of the object to be inspected is 0 degrees. When the object rotation is 45 degrees, the detector 5' detects the radiation passed through the object along a line IN2-OUT2. When the object is rotated by one turn around its rotary center O, the detector 5' detects the radiation tangential to a circle P having a radius r1. Similarly the other detectors 1' to 15' detect the radiation tangential to a plurality of concentric circles having different radii, as shown in FIG. 1C. Spacings between the adjacent concentric circles correspond to those between the detectors. This means that the narrower the spacings are the higher the spatial resolution is. When the spacings are not the same, this causes generation of noise called artifact in an image and thus it is important to provide substantially an identical spacing for the detectors.

Figure 1D:
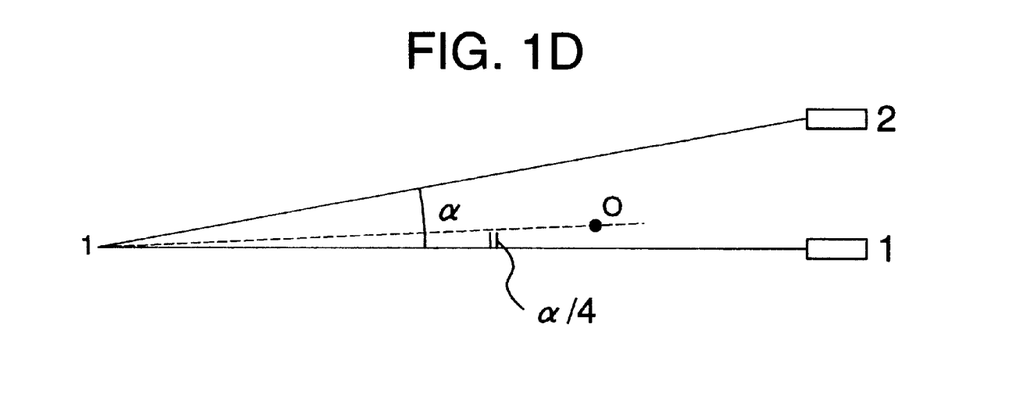

Explanation will next be made as to a relationship between the spacing between the concentric circles and the rotary center of the checking object. The respective detectors 8 are arranged with an angle pitch of an angle $\alpha$ (radians) with respect to the X ray source 1 as shown in FIG. 1D. In this connection, D (mm) denotes a distance between the rotary center O of the rotary table and the X ray source 1. With such an arrangement of the X ray CT system, in order that the spacings between the concentric circles made with respect to the respective X ray detectors 8 of the array detection device 6 are the smallest and the same, it is required that the rotary center O is located between a line connecting the detector 1' of the X ray detectors 8 and the X ray source 1 and a line connecting the detector 2' of the detectors 8 adjacent to the detector 1' and the X ray source 1, and at a position where the angle $\alpha$ of an angular pitch is interiorly divided in a ratio of 1:4. The detectors i (i=number between 1' and 15') of the detectors 8 in FIG. 1A correspond to radius R(i) of the corresponding concentric circle and the radius R(i) is expressed as follows, when the number i is odd.

$$R(i)=D\times\sin(\alpha/4+j\times\alpha) \quad (1)$$

When the number i is even, the radius R(i) is expressed as follows.

$$R(i)=D\times\sin(3\alpha/4+j\times\alpha) \quad (2)$$

Where j is an integer part of (i−1)/2. A maximum in the spacings between the adjacent concentric circles is a spacing $\Delta R1$ between the circle of the X ray detector 1' of the detectors 8 and the circle of the X ray detector 2' thereof, and is expressed as follows.

$$\Delta R1=D\times\{\sin(3\times\alpha/4)-\sin(\alpha/4)\} \quad (3)$$

When $\alpha$ is much smaller than 1, $\sin\alpha\approx\alpha$ and $\Delta R1$ can be approximated as follows.

$$\Delta R1=D\times\alpha/2 \quad (4)$$

In order to increase the spatial resolution of a tomographic image, it is necessary to make small the spacing of the concentric circles made by the array detection device 6. To this end, thus, it is required to make the angle $\alpha$ small according to the equation (4) or to make small the distance D between the X ray source 1 and the rotary center of the rotary table. However, making the angle $\alpha$ small is limited by the physical sizes of the respective X ray detectors 8. On the other hand, making small the distance D between the X ray source 1 and the rotary center O of the rotary table causes the possible size of the object 14 covered with the radial X ray becomes small.

Explanation will then be made as to how to increase the spatial resolution of a tomographic image without causing reduction of the possible image size of the object 14. In the above tomography method, the rotary table is rotated by one turn in order to obtain a single tomographic image. Consider now a case where a single tomographic image is obtained by rotating the rotary table by two turns. In this case, the position of the rotary center O of the rotary table for the first turn is made different from that for the second turn. More specifically, assuming that the rotary center O for the first turn is located at a position where the angle $\alpha$ of an angular pitch is interiorly divided in a ratio of 1:7 and the rotary center O for the second turn is located at a position where the angle $\alpha$ of the angular pitch is interiorly divided in a ratio of 3:5, then radius R1(i) of concentric circle made by the array detection device 6 for the first turn is expressed as follows, when the detectors 8 are denoted by odd numbers i.

$$R1(i)=D\times\sin(\alpha/8+j\times\alpha) \quad (5)$$

Figure 2:
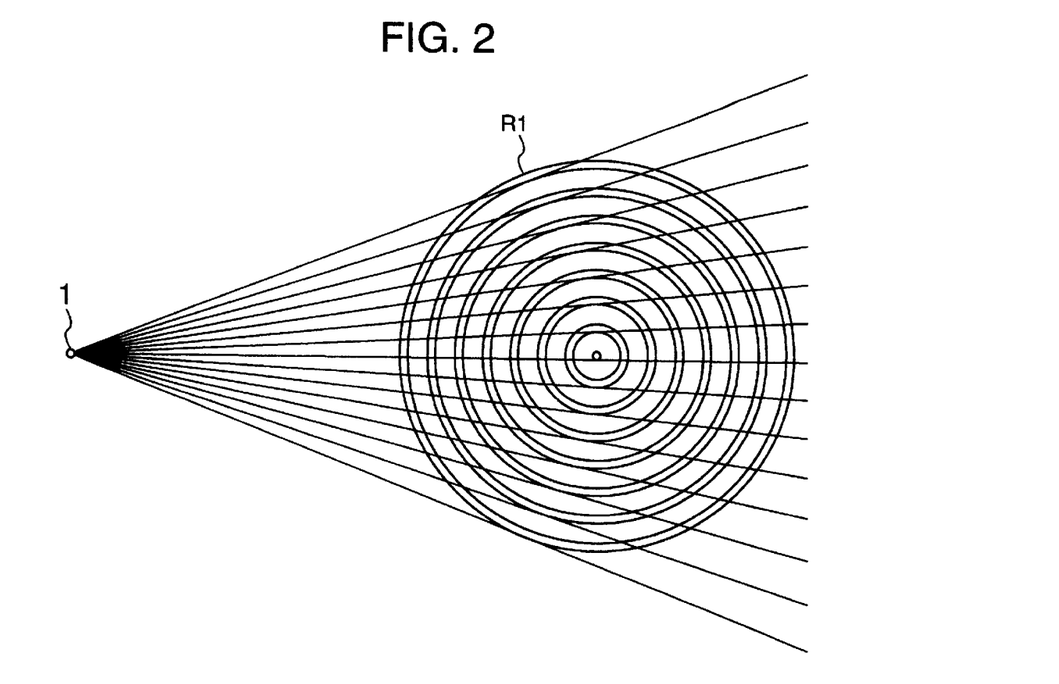
FIG. 2 shows concentric circles obtained when a rotary center is set at a point where an angle $\alpha$ is interiorly divided in a ratio of 1:7.

When the detectors 8 are denoted by even numbers i, the radius R1(i) is expressed as follows.

$$R1(i)=D\times\sin(7\times\alpha/8+j\times\alpha) \quad (6)$$

where j denotes an integer part of (i−1)/2. The radius R1(i) of concentric circle is illustrated in FIG. 2. Radius R2(i) of concentric circle made by the array detection device 6 for the second turn is expressed as follows, when the detectors 8 are denoted by odd numbers i.

$$R2(i)=D\times\sin(3\times\alpha/8+j\times\alpha) \quad (7)$$

Figure 3:
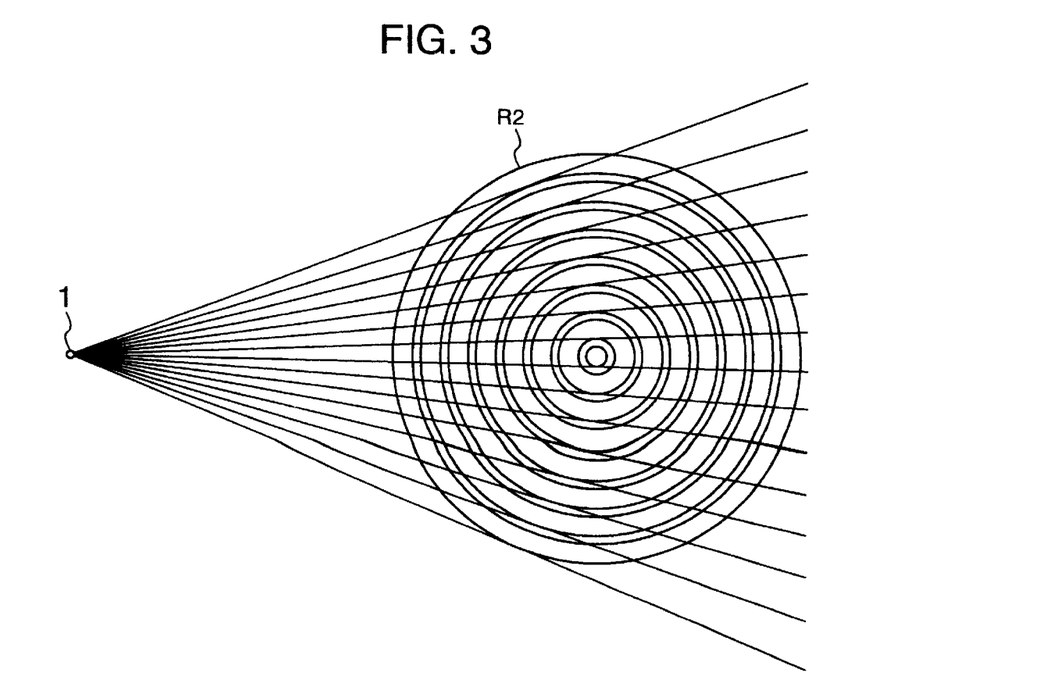
FIG. 3 shows concentric circles obtained when the rotary center is set at a point where the angle $\alpha$ is interiorly divided in a ratio of 3:5.

When the detectors 8 are denoted by even numbers i, the radius R2(i) is expressed as follows.

$$R2(i)=D\times\sin(5\times\alpha/8+j\times\alpha) \quad (8)$$

where j denotes an integer part of (i−1)/2. The concentric circles are illustrated in FIG. 3.

Figure 4:
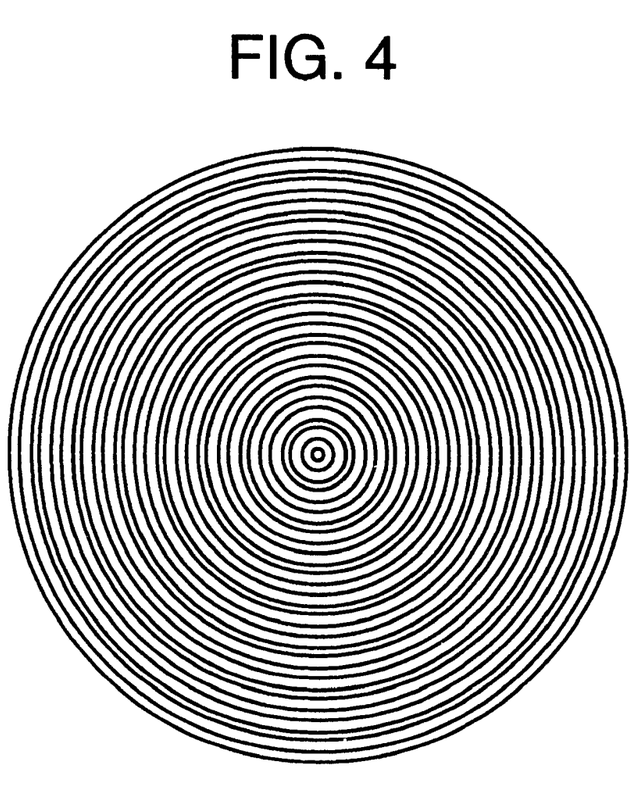
FIG. 4 shows concentric circles obtained when the circles of FIG. 2 are combined with those of FIG. 3.

When the concentric circles obtained for the first turn are combined with those obtained for the second turn, such concentric circles as shown in FIG. 4 are obtained. With respect to the concentric circles, largest one of the spacings between the concentric circles is a spacing $\Delta R2$ between the concentric circle of the X ray detector 1' of the detectors 8 for the first turn and the concentric circle of the X ray detector 1' of the detectors 8 for the second turn. The spacing $\Delta R2$ is expressed as follows.

$$\Delta R2=D\times\{\sin(3\times\alpha/8)-\sin(\alpha/8)\} \quad (9)$$

When α is much smaller than 1, the spacing ΔR2 can be approximated as:

$$\Delta R2 = D \times \alpha/4 \quad (10)$$

When the concentric circles obtained according to the equation (10) are compared with those obtained according to the equation (4), the spacing of the concentric circles according to the equation (10) is ½ of that according to the equation (4).

The same can be applied to the third, fourth, . . . turns. When it is desired to obtain a single tomographic image by N turns (N being integer of 2 or more), the rotary center O for the m-th turn (m=1, 2, . . . , and N) is located at a position where the angle a of an angle pitch is interiorly divided in a ratio of (2m−1):(4N−2m+1). In this case, the spacing of the concentric circles obtained by the array detection device 6 by the N turns is 1/N of the spacing by the one turn. In this way, for obtaining a tomographic image in a single transversal plane, the object to be checked is rotated by a plurality of turns and the position of the rotary center O is shifted sequentially in the array direction of the X ray detectors for every turn, so that the spatial resolution of the tomographic image can be increased without narrowing the array pitch of the X ray detectors.

Figure 6:
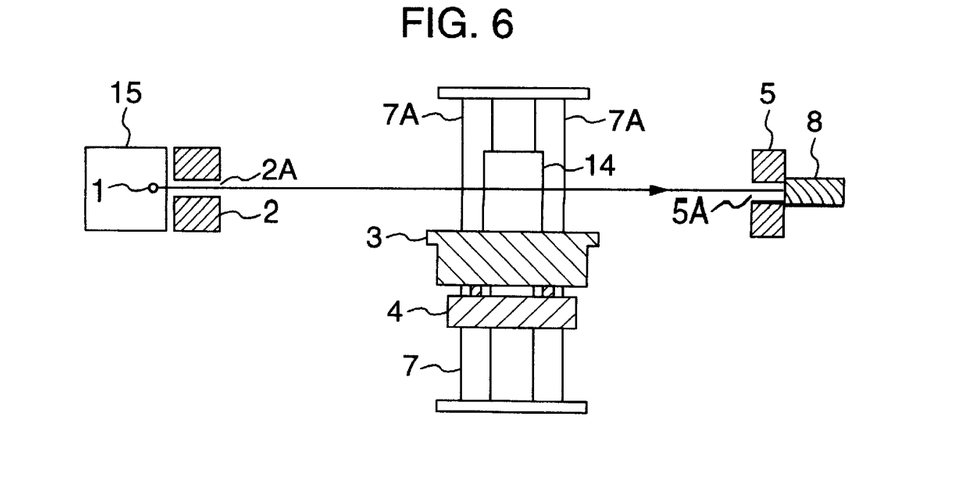
FIG. 6 shows a vertical cross-sectional view of FIG. 5.
Figure 7:
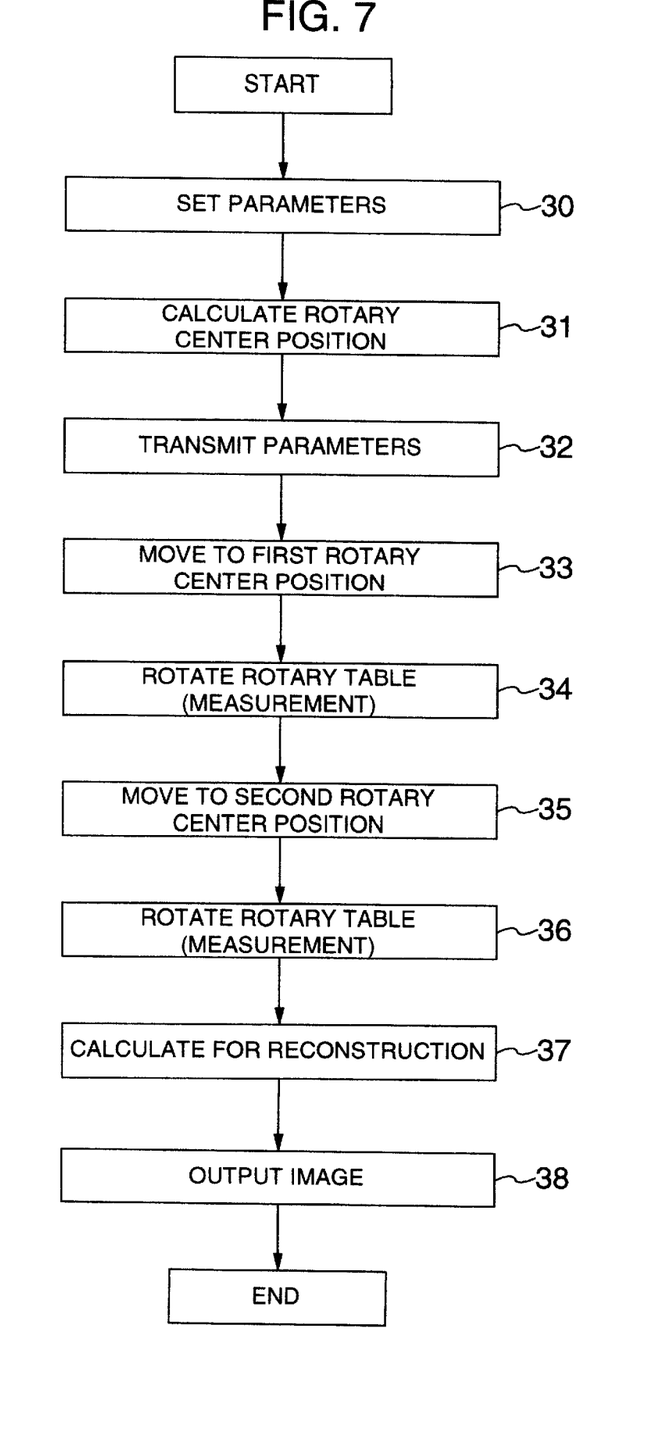
FIG. 7 is a flowchart for explaining how to obtain a tomographic image in the embodiment of FIG. 5.

A preferred embodiment of the present invention will be explained by referring to FIGS. 5, 6 and 7. FIG. 6 is a vertical cross-sectional view of FIG. 5. The present embodiment includes an X ray source 15, a precollimator 2, a rotary table 3, a translation device 4, a collimator 5, an array detection device 6, a rotary table moving up/down device 7, an X ray source control device 16, a motion mechanism controller 17 for controlling motions such as rotation, translation and up/down movements of the rotary table, a detection circuit 18, a computer 19, an input device 20, and a display unit 21.

The X ray source 15 has an X ray source 1 for generating an X ray, and emission and stoppage of the x ray from the X ray source 15 are controlled by the X ray source control device 16. The X ray source 1 in the X ray source 15 may be, for example, an X ray tube or an electron beam type accelerator. The precollimator 2 is made of material having an ability of shielding the X ray such as lead or tungsten, and has a window 2A which causes the X ray to have a fan (or sector) beam shape.

The array detection device 6 is made up of a multiplicity of X ray detectors 8 arranged in a row. The detectors 8 are X ray detectors or semiconductor detectors which include scintillators and photodiodes in combination. The collimator 5, which is disposed in a side of the array detection device 6 in which the X ray source 15 is provided, is made of material having a high X-ray shielding ability such as lead or tungsten. The collimator S is formed therein with a multiplicity of slits 5A. The detectors 8 are positioned as opposed to the associated slits 5A. The collimator 5 functions to prevent the X ray scattered by the object 14 from entering the detectors 8. The slits 5A are all directed toward the direction of the X ray source 1 and determines the X ray directions incident to the detectors 8.

The rotary table 3, on which the object 14 is mounted, has a drive device for rotating the table. The rotation of the rotary table 3 causes start of taking a tomographic image of the object 14. The translation device 4 functions to move the rotary table 3 in an X direction. The rotary table moving up/down device 7 is used to move up or down the translation device 4. More in detail, the rotary table moving up/down device 7 has four rotary screws 7A which are rotated by a motor and are extended vertically. The rotary screws 7A are engaged with a table of the translation device 4. The driving operations of the rotary table 3, translation device 4 and rotary table moving up/down device 7 are controlled by control signals issued from the motion mechanism controller 17. The motion mechanism control device 17, when the rotary table 3 is rotated, generates a pulse for each set rotary angle of the rotary table 3. The pulses are used as a trigger signal for X ray generation and as a gate signal for the detection circuit 18 to take in the detection signals from the detectors 8. The above pulse as the trigger signal for X ray generation is sent from the motion mechanism controller 17 to the X ray source control device 16. The pulse as the gate signal for input of the detection signals from the respective X ray detectors 8 is sent from the motion mechanism controller 17 to the detection circuit 18.

The detection circuit 18 amplifies the analog detection signals received from the X ray detectors 8, convert them to digital signals and then outputs them to the computer 19. The computer 19 creates a tomographic image through predetermined operations on the basis of the received digital detection signals. The obtained tomographic image is displayed on the display unit 21 and may be printed by a printer (not shown) as necessary.

How to obtain a tomographic image in the present embodiment will be explained with reference to a flowchart of FIG. 7. The flowchart corresponds to how to obtain a tomographic image in one transversal plane of the object 14 by rotating the rotary table 3 by two turns. It is assumed that a height of the tomographic transversal plane of the object 14 corresponds to a height from the rotary table 3 to a position 100 mm high thereabove. An operator sets various parameters necessary for taking a tomographic image of the object 14 (step 30). The parameters include the height position (100 mm in the present example) of the tomographic transversal plane and the number of rotational turns (two turns in this example) necessary for taking a tomographic image in one transversal plane. The operator enters these parameters into the computer 19 from the input device 20. The computer 19 calculates, with use of the parameters set in the step 30, a rotary center position of the rotary table 3 for the first turn and a rotary center position thereof for the second turn (step 31). As has been mentioned above, the rotary center of the rotary table 3 for the first rotational turn is located at a position where the angle α is internally divided in a ratio of 1:7, while the rotary center of the rotary table 3 for the second rotational turn is located at a position where the angle α is internally divided in a ratio of 3:5. The computer 19 outputs the set height position of the tomographic transversal plane and the rotary center positions of the first and second turns calculated in the step 31 to the motion mechanism controller 17 (step 32).

The motion mechanism controller 17, on the basis of the rotary center position of the first turn, controls the translation device 4 to cause the rotary table 3 to be moved to the rotary center position of the first turn by the driving of the translation device 4 (step 33). In a step 33, the motion mechanism controller 17 controls the rotary table moving up/down device 7 (more specifically, its motor) in such a manner that rotation of the rotary screws 7A cause the rotary table 3 to be vertically moved up or down, whereby the tomographic transversal plane of the object 14 is set at the set height position.

Thereafter the rotary table 3 is rotated for measurement and for collection of the detection signals by the detection circuit 18 (step 34). More specifically, the measurement is carried out in such a manner as to be mentioned below. The motion mechanism controller 17 outputs a control signal to rotate the rotary table 3. The motion mechanism controller 17, when th e rotary table 3 is rotated, generates a pulse for each set rotational angle of the rotary table 3. The pulse is sent to the X ray source control device 16 as a trigger signal for X ray generation. The X ray source control device 16, when receiving the trigger signal, issues a signal to the X ray source 1 to cause the X ray source 1 to emit an X ray. The X ray is passed through the transversal plane of the object 14 having a set height position and then detected by the respective X ray detectors 8. The X ray detectors 8 output their detection signals. The above pulse is sent from the motion mechanism controller 17 to the detection circuit 18 as the gate signal for receiving the detection signals. The detection circuit 18, when receiving the gate signal, receives the detection signals from the respective X ray detectors 8. The detection circuit 18 amplifies the analog detection signals, converts them to digital signals, and sends the digital signals to the computer 19. The above operations are repeated until the rotary table 3 rotates by one turn. When the rotary table 3 is rotated by one turn, the measurement of the object 14 for the first turn is completed. Since synchronism between the emission of the X ray from the X ray source 1 and the collection of the detection signals by the detection circuit 18 is achieved by the pulse generated for each set rotational angle, the detection signals of the X ray passed through the object 14 can be efficiently collected. Further, since the emission of the X ray is controlled based on the pulse (trigger signal) generated for each set rotational angle, useless emission of the X ray can be avoided.

After the completion of the first turn measurement, the motion mechanism controller 17, on the basis of the rotary center position of the second turn, moves the rotary table 3 to the rotary center position of the second turn as in the step 33 (step 35). Since the height position of the tomographic transversal plane of the object 14 for the second turn is the same as that for the first turn, no control of adjustment of the height position of the tomographic transversal plane in the step 34 is carried out. The rotary table 3 is rotated by one turn so that, similarly to the step 34, the detection circuit 18 collects the detection signals and applies the collected signals to the computer 19 (step 36).

On the basis of the digital signals of the digital signals (after subjected to the amplifying operation and analog/digital conversion) received from the X ray detectors 8 in the steps 34 and 46, the computer 19 performs reconstructing operation of a tomographic image in the tomographic transversal plane of the object 14 at one set height position (step 37). The computer 19 is also means for performing reconstructing operation of the tomographic image. The reconstructed tomographic image is sent from the computer 19 to the display unit 21 (step 38). The above mentioned operations are repeated at a plurality of heights at which the tomographic images of the object 14 are desired.

The operations of the steps 37 and 38 may be carried out after completion of the operations of the steps 30 to 36 for the plurality of heights of the object 14. Thereby tomographic images in transversal planes of the object 14 can also be obtained.

In the present embodiment, the rotary table 3 is rotated with the rotary center position shifted with respect to one transversal plane of the object 14, so that the tomographic image of the object 14 in the transversal plane can be reconstructed by using the digital signals issued from the X ray detectors 8 through a plurality of rotational turns (two turns in the present embodiment). Accordingly, in accordance with the present embodiment, the spatial resolution of the tomographic image can be increased without causing reduction of the angular pitch of the X ray detectors 8.

An X ray CT system in accordance with another preferred embodiment of the present invention will be explained with use of FIGS. 8, 9 and 10. FIG. 9 is a vertical cross sectional view of FIG. 8. The present embodiment is arranged so that the X ray source 15, collimator 5 and array detection device 6 can resolve around the object 14 without causing rotation of the object 14.

A pivoting truck 22 having wheels carries on its upper surface a translation device 25 of an X ray source 15 and a translation device 26 of a collimator 5 and an array detection device 6. A moving truck 23 undergoing translating movement by means of the translation device 25 carries the X ray source 15 and precollimator 2 thereon. A moving truck 24 undergoing translating movement by means of the translation device 26 carries the collimator 5 and array detection device 6 thereon. A stationary table 3A is provided on a longitudinal table 27. The center of the stationary table 3A coincides with the pivotal center of the pivoting truck 22. The object 14 to be inspected is mounted on the stationary table 3A. A table moving up/down device 7B has four rotary screws 7A which are rotably driven by a motor and are vertically extended. The rotary screws 7A are meshed with the longitudinal table 27.

Figure 5:
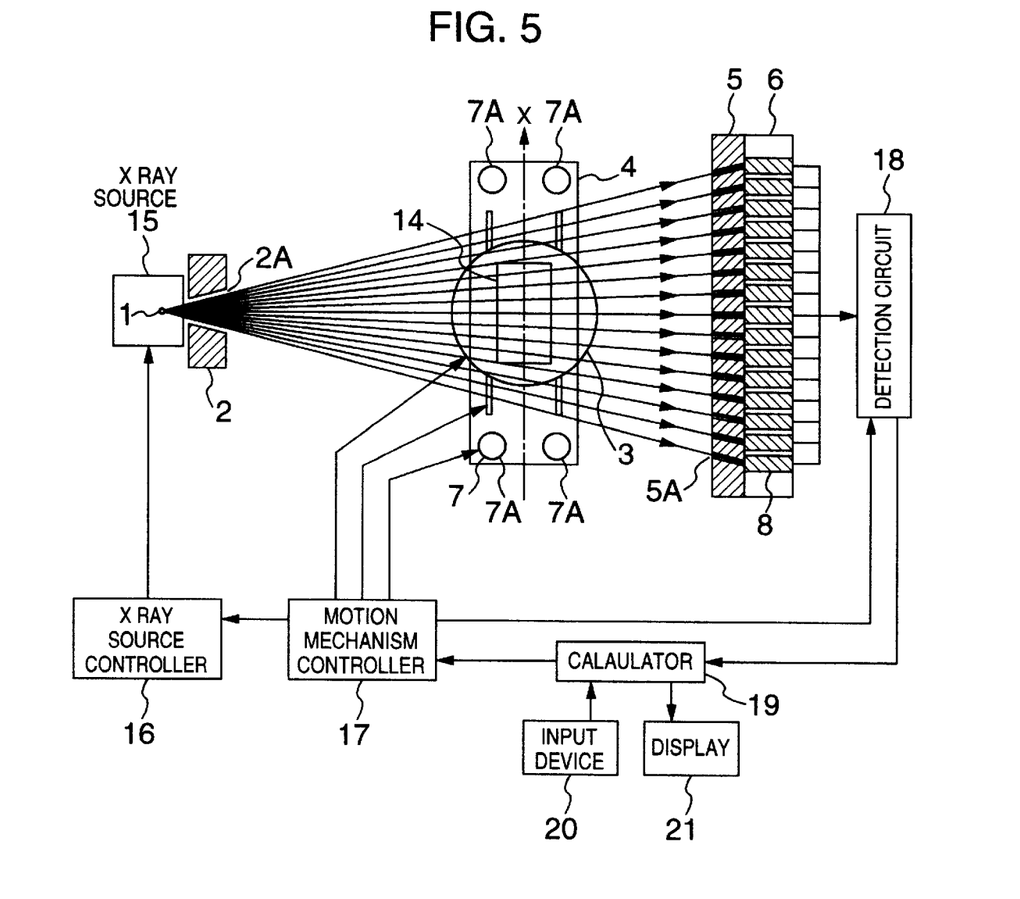
FIG. 5 shows an X ray CT system in accordance with an embodiment of the present invention.

Though not illustrated, even the present embodiment includes the motion mechanism controller 17, detection circuit 18, computer 19, input device 20 and display unit 21, as in the embodiment of FIG. 5. In the present embodiment, a tomographic image in a transversal plane of the object 14 is taken by pivoting the pivoting truck 22. In the present embodiment, the motion mechanism controller 17 controls the pivoting truck 22 and translation devices 25 and 26.

Figure 8:
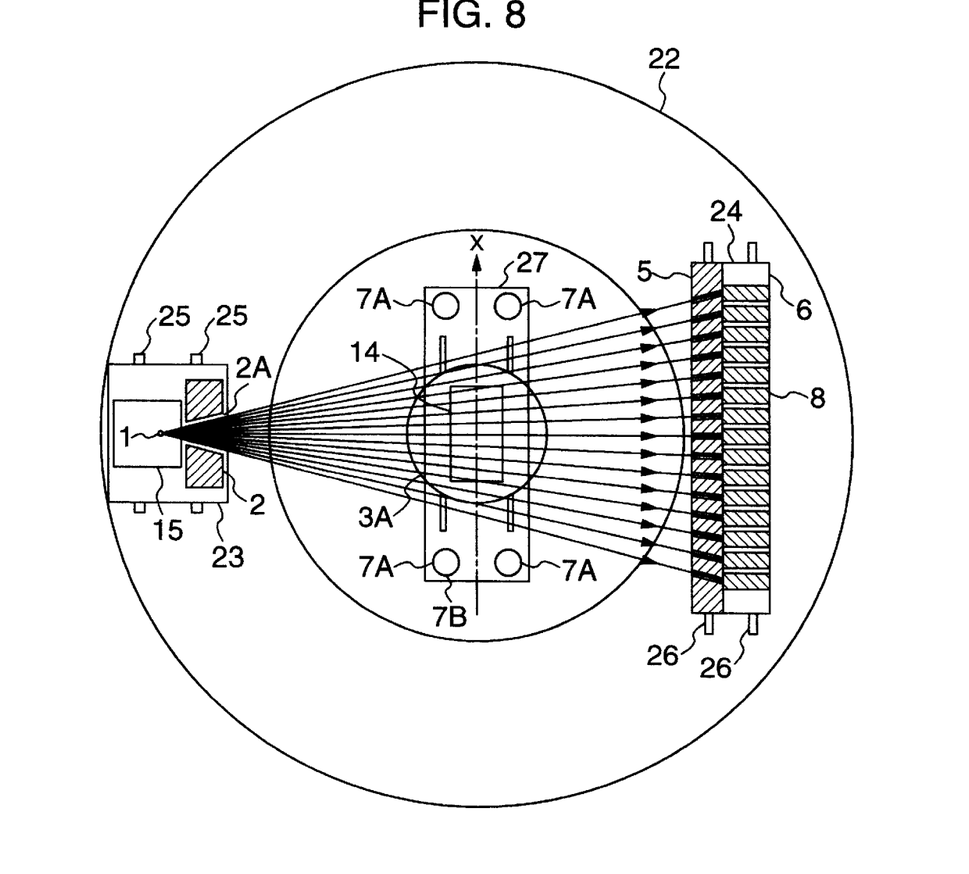
FIG. 8 shows an X ray CT system in accordance with another embodiment of the present invention.
Figure 9:
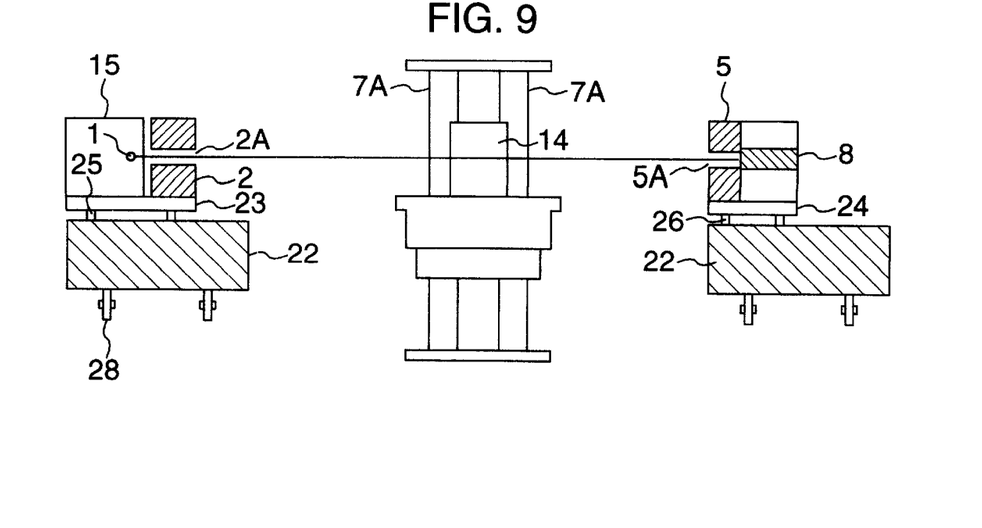
FIG. 9 shows a vertical cross-sectional view of FIG. 8.
Figure 10:
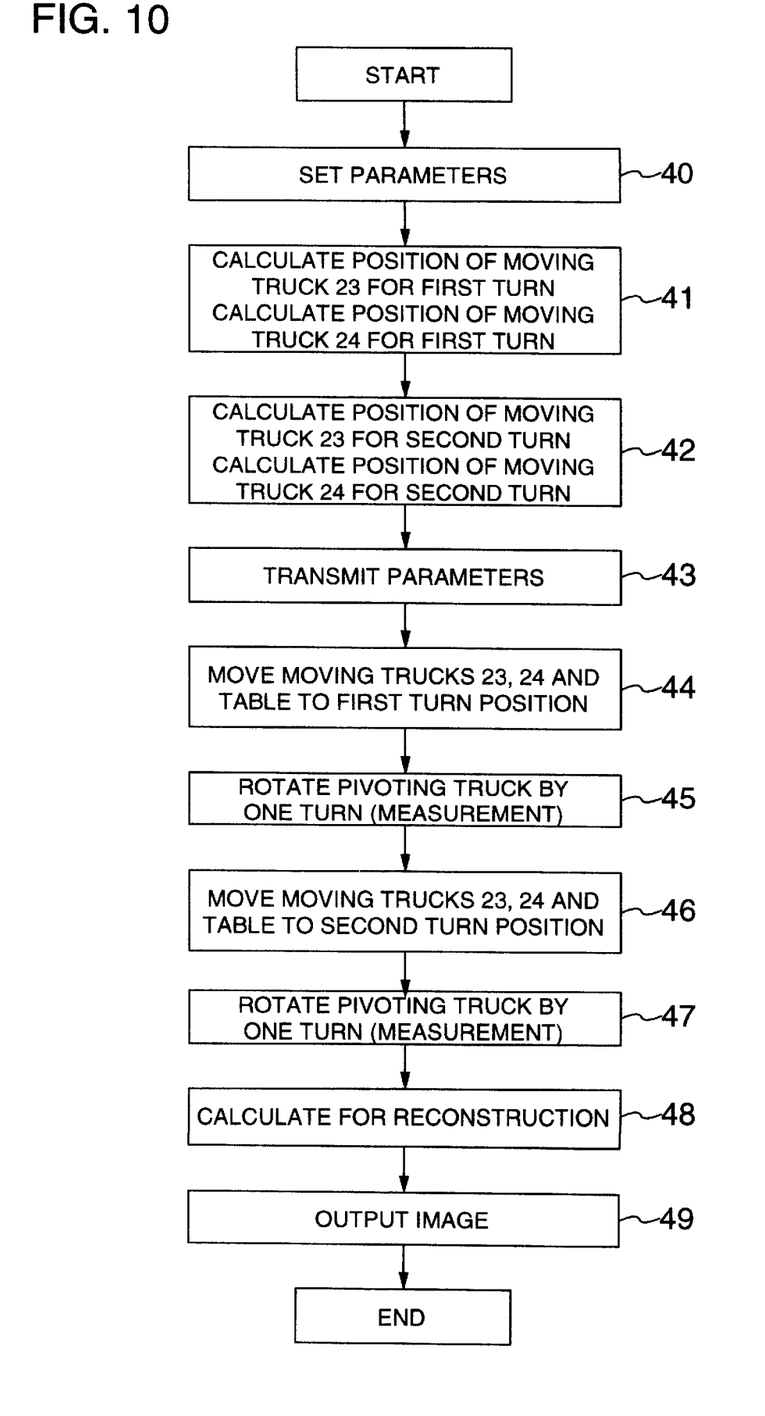
FIG. 10 is a flowchart for explaining how to obtain a tomographic image in the embodiment of FIG. 8.

FIG. 10 is a flowchart for explaining operations when a tomographic image is taken with use of the system of FIG. 8.

In a step 40, the operator enters parameters such as a height of a tomographic transversal plane and the number of turns in the pivoting truck necessary for taking a picture of a tomographic image in one transversal plane.

In a step 41, the computer calculates positions of the moving trucks 23 and 24 for the first turn.

In a step 42, the computer calculates positions of the moving trucks 23 and 24 for the second turn.

This substantially means to calculate positions of the X ray source 15 and precollimator 2 and positions of the collimator 5 and array detection device 6 for the first and second turns. The positions are positions of the longitudinal table in its longitudinal direction (X direction) and are relative positions with respect to the center position of the stationary table 3A. The positions of the moving trucks 23 and 24 for the first turn are set so that the angle α of an angular pitch is interiorly divided in a ratio of 1:7 by the center position of the stationary table 3A, whereas the positions of the moving trucks 23 and 24 for the second turn are set so that the angle α of an angular pitch is interiorly divided in a ratio of 3:5 by the center position of the stationary table 3A.

In a step 43, the calculated results are sent to the motion mechanism controller 17.

In a step 44, the motion mechanism controller 17 drives the translation devices 25 and 26 to move the moving trucks 23 and 24 to the first turn positions. The table moving up/down device 7B vertically moves the stationary table 3A in such a manner that the tomographic transversal plane of the object 14 comes at the set height position.

In a step 45, radiation is irradiated on the object to be inspected during one turn of the pivoting truck 22 to perform its measurement. In this case, the detection circuit 18 collects the digital signals.

In a step 46, the motion mechanism controller 17 drives the translation devices 25 and 26 to move the moving trucks 23 and 24 to the second turn positions.

In a step 47, radiation is irradiated on the object to be inspected during one turn of the pivoting truck 22 to perform its measurement, as in the first turn case.

In a step 48, image data obtained for the second turn are reconstructed into a single tomographic image and then displayed on the display unit (step 49).

In accordance with the present embodiment, since the pivoting truck 22 is pivoted with the positions of the moving trucks 23 and 24 shifted with respect to the center position of the stationary table 3A for one transversal plane of the object 14, the digital signals issued from the X ray detectors 8 obtained for a plurality of turns (two turns in the present embodiment) of the pivoting truck 22 are used to reconstruct the digital signal into a tomographic image in the transversal plane of the object 14. Thus, the present embodiment can increase the spatial resolution of the tomographic image without the need for narrowing the angular pitch of the X ray detectors 8.

The present invention is not limited to the above specific embodiments, and it should be appreciated that various modifications and variations within the scope and spirit of the attached claims are also included in the present invention.

What is claimed is:

1. A computerized tomography system comprising:

a radiation source;

a plurality of radiation detectors arranged so as to be opposite to said radiation source, said radiation detectors being arranged so that any two adjacent radiation detectors are viewed from said radiation source with a viewing angle of $\alpha$ radians;

a table located between said radiation source and said plurality of said radiation detectors on which an object to be inspected is laid;

a moving apparatus for changing a relative positional relationship between said radiation source and said table in a linear direction across radiations irradiated from said radiation source;

a controller for driving said moving apparatus every m rotational turns so that when said radiation source and radiation detectors and said table are relatively rotated by a total of N turns (N being an integer of 2 or more) to irradiate radiations to said object to be inspected on said table, a position of a relative rotation center of said radiation source and radiation detectors and said table at an m-th turn (m=1, 2, ... and N) is located on a point where said viewing angle $\alpha$ is internally divided in a ratio of $(2m-1):(4N-2m+1)$ in said linear direction; and a tomographic image reconstruction unit for reconstructing a tomographic image of said object to be inspected from radiation transmission data of said object to be inspected which are detected by a plurality of said radiation detectors every one relative rotational turn of said radiation source and radiation detectors and said table at each of different positions of said relative rotation center during the N turns.

2. A computerized tomography system comprising:

a radiation source for irradiating radiations on an object to be inspected;

a rotation table for carrying said object thereon to rotate said object;

a moving apparatus for moving said rotation table in a predetermined linear direction;

a collimator having a plurality of through-holes for passage of said radiations passed through said object;

a plurality of radiation detectors arranged so as to be opposite to said through-holes for detecting the radiations passed through said through-holes, said radiation detectors being arranged so that any two adjacent radiation detectors are viewed from said radiation source with a viewing angle of $\alpha$ radians;

a controller for driving said moving apparatus every m rotational turns so that when said rotation table is rotated by a total of N turns (N being an integer of 2 or more) to irradiate radiations from said radiation source to said object to be inspected on said rotation table, a position of a rotation center of said table at an m-th turn (m=1, 2, ..., and N) is located on a point where said viewing angle $\alpha$ is internally divided in a ratio of $(2m-1):(4N-2m+1)$ in said linear direction; and a tomographic image reconstruction unit for reconstructing a tomographic image of said object to be inspected from radiation transmission data of said object to be inspected which are detected by a plurality of said radiation detectors every one rotational turn of said table at each of different positions of said rotation center during the N turns.

3. A computerized tomography system comprising:

a pivoting truck;

a radiation source provided on said pivoting truck for irradiating radiations on an object to be inspected;

a table disposed inside of said pivoting truck for mounting said object thereon;

a collimator provided on said pivoting truck and having a plurality of through-holes for passage of said radiations passed through said object;

a plurality of radiation detectors disposed on said pivoting truck so as to be opposite to said through-holes for detecting said radiations passed through said through-holes, said radiation detectors being arranged so that any two adjacent radiation detectors are viewed from said radiation source with a viewing angle of $\alpha$ radians;

a moving apparatus for moving said radiation source, collimator and said radiation detectors in a predetermined linear direction;

a controller for driving said moving apparatus every m rotational turns so that when said pivoting truck is rotated by a total of N turns (N being an integer of 2 or more) to irradiate radiations from said radiation source to said object to be inspected on said table, a position of a rotation center of said pivoting truck at an m-th turn (m=1, 2, ..., and N) is located on a point where said viewing angle $\alpha$ is internally divided in a ratio of $(2m-1):(4N-2m+1)$ in said linear direction; and a tomographic image reconstruction unit for reconstructing a tomographic image of said object to be inspected from radiation transmission data of said object to be inspected which are detected by a plurality of said radiation detectors every one rotational of said pivoting truck at each of different positions of said rotation center during the N turns.

4. A computerized tomography method in a computerized tomography system including a radiation source, a plurality of radiation detectors arranged so as to be opposite to said radiation source, said radiation detectors being arranged so that any two adjacent radiation detectors are viewed from said radiation source with a viewing angle of $\alpha$ radians, a table located between said radiation source and said plurality of radiation detectors on which an object to be inspected is laid, a moving apparatus for changing a relative positional relationship between said radiation source and said table in a linear direction across radiations irradiated from said radiation source, comprising the steps of:

detecting radiations transmitted through said object to be inspected by said plurality of radiation detectors by irradiating radiations from said radiation source to said object to be inspected on said table and by relatively rotating said radiation source and radiation detectors and said table by a total of N turns (N being an integer of 2 or more), said step of detecting radiations comprising a step of driving said moving apparatus every m rotational turns so that a position of a relative rotation center of said radiation source and radiation detectors and said table at an m-th turn (m=1, 2, ..., and N) is located on a point where said viewing angle $\alpha$ is internally divided in a ratio of $(2m-1):(4N-2m+1)$ in said linear direction; and reconstructing a tomographic image of said object to be inspected from radiation transmission data of said object to be inspected which are detected by a plurality of said radiation detectors every one relative rotational turn of said radiation source and radiation detectors and said table at each of different positions of said relative rotation center during the N turns.

5. A computerized tomography method in a computerized tomography system including a radiation source for irradiating radiations on an object to be inspected; a rotation table for carrying said object thereon to rotate said object; a moving apparatus for moving said rotation table in a predetermined linear direction; a collimator having a plurality of through-holes for passage of said radiations passed through said object; and a plurality of radiation detectors arranged so as to be opposite to said through-holes for detecting the radiations passed through said through-holes, said radiation detectors being arranged so that any two adjacent radiation detectors are viewed from said radiation source with a viewing angle of $\alpha$ radians, comprising the steps of:

detecting radiations transmitted through said object to be inspected by said plurality of radiation detectors by irradiating radiations from said radiation source to said object to be inspected on said table and by rotating said rotation table by a total of N turns (N being an integer of 2 or more), said step of detecting radiations including a step of driving said moving apparatus every m rotational turns so that a position of a rotation center of said rotation table at an m-th turn (m=1, 2, ..., and N) is located on a point where said viewing angle $\alpha$ is internally divided in a ratio of $(2m-1):(4N-2m+1)$ in said linear direction; and reconstructing a tomographic image of said object to be inspected from radiation transmission data of said object to be inspected which are detected by said plurality of radiation detectors every one rotational turn of said rotation table at each of different positions of said rotation center during the N turns.

6. A computerized tomography method for a computerized tomography system comprising a pivoting truck; a radiation source provided on said pivoting truck for irradiating radiations on an object to be inspected; a table disposed inside of said pivoting truck for mounting said object thereon; a collimator provided on said pivoting truck and having a plurality of through-holes for passage of said radiations passed through said object; a plurality of radiation detectors arranged on said pivoting truck so as to be opposite to said through-holes for detecting said radiations passed through said through-holes, said radiation detectors being arranged so that any two adjacent radiation detectors are viewed from said radiation source with a viewing angle of $\alpha$ radians; and a moving apparatus for moving said radiation source, collimator and radiation detectors in a predetermined linear direction, comprising the steps of:

detecting radiations transmitted through said object to be inspected by said plurality of radiation detectors by irradiating radiations from said radiation source to said object to be inspected on said table and by rotating said pivoting truck by a total of N turns (N being an integer of 2 or more), said step of detecting radiations comprising a step of driving said moving apparatus every m rotational turns so that a position of a rotation center of said pivoting truck at an m-th turn (m=1, 2, ..., and N) is located on a point where said viewing angle $\alpha$ is internally divided in a ratio of $(2m-1):(4N-2m+1)$ in said linear direction; and reconstructing a tomographic image of said object to be inspected from radiation transmission data of said object to be inspected which are detected by said plurality of radiation detectors every one rotational turn of said pivoting truck at each of different positions of said rotation center during the N turns.

* * * * *